(12) United States Patent
Bonnert et al.

(10) Patent No.: US 6,555,341 B1
(45) Date of Patent: Apr. 29, 2003

(54) HUMAN THETA SUBUNIT OF THE GABA$_A$ RECEPTOR

(75) Inventors: Timothy Peter Bonnert, Much Hadham (GB); Paul John Whiting, Stansted Mountfitchet (GB)

(73) Assignee: Merck Sharp & Dohme Ltd., Hoddeson (GB)

( * ) Notice: Subject to any disclaimer, the term of this patent is extended or adjusted under 35 U.S.C. 154(b) by 0 days.

(21) Appl. No.: 09/403,667

(22) PCT Filed: Apr. 24, 1998

(86) PCT No.: PCT/GB98/01206

§ 371 (c)(1),
(2), (4) Date: Oct. 25, 1999

(87) PCT Pub. No.: WO98/49293

PCT Pub. Date: Nov. 5, 1998

(30) Foreign Application Priority Data

Apr. 25, 1997 (GB) .............................................. 9708479

(51) Int. Cl.[7] ........................ C07K 21/04; C12N 15/00; C12N 5/00; C12N 15/03; C12N 15/06
(52) U.S. Cl. ................... 435/69.1; 435/366; 435/320.1; 435/252.3; 435/325; 536/23.5; 536/23.1
(58) Field of Search ............................ 435/69.1, 320.1, 435/252.3, 7.1, 35, 325, 366; 536/23.5, 23.1; 530/350

(56) References Cited

FOREIGN PATENT DOCUMENTS

WO  WO 94/13799  6/1994
WO  WO 95/29234  11/1995

OTHER PUBLICATIONS

Lehmann–Horn, F., et al., 1999, Physiol Rev 79(4): 1317–1372.*

Oelmann, S., et al., 2001., J. Biol. Chem. 28(13): 26291–26300.*

Ymer, et al., "GABAA Receptor Beta Subunit Heterohene-ity: Functional Expression of Cloned cDNAs", Embo. Journal, vol. 8, No. 6, 1989, pp. 1665–1670.

Levin, et al., EMBL Database Entry HSU47334, Accession No. U47334, Jul. 7 1996.

Marra, et al., "The WashU–HHMI Mouse EST Project", DMBL Database Entry MM7808, Accession No. W15780, May 4 1996.

Bateson, et al., "Gamma–Aminobutyric Acid–A Receptor Heterogeneity is Increased By Alternative Splicing . . . ", EMBL Database Entry GDGRB4M, Accession No. X56648.

* cited by examiner

*Primary Examiner*—Elizabeth Kemmerer
*Assistant Examiner*—Sandra Wegert
(74) *Attorney, Agent, or Firm*—Michael D. Yablonsky; Jack L. Tribble

(57) ABSTRACT

This invention concerns the cloning of a novel cDNA sequence encoding a particular subunit of the human GABA$_A$ receptor. In addition, the invention relates to a stable cell line capable of expressing said cDNA and to the use of the cell line in a screening technique for the design and development of subtype-specific medicaments.

24 Claims, 6 Drawing Sheets

Human θ Subunit

```
  1 ATGCTGCGAGCCGCAGTGATCCTGCTGCTCATCAGGACCTGGCTCGCGGAGGGCAACTAC   60
    M  L  R  A  A  V  I  L  L  L  I  R  T  W  L  A  E  G  N  Y

61 CCCAGTCCCATCCCGAAATTCCACTTCGAGTTCTCCTCTGCTGTGCCCGAAGTCGTCCTG  120
    P  S  P  I  P  K  F  H  F  E  F  S  S  A  V  P  E  V  V  L

121 AACCTCTTCAACTGCAAAAATTGTGCAAATGAAGCTGTGGTTCAAAAGATTTTGGACAGG  180
    N  L  F  N  C  K  N  C  A  N  E  A  V  V  Q  K  I  L  D  R

181 GTGCTGTCAAGATACGATGTCCGCCTGAGACCGAATTTTGGAGGTGCCCCTGTGCCTGTG  240
    V  L  S  R  Y  D  V  R  L  R  P  N  F  G  G  A  P  V  P  V

241 AGAATATCTATTTATGTCACGAGCATTGAACAGATCTCAGAAATGAATATGGACTACACG  300
    R  I  S  I  Y  V  T  S  I  E  Q  I  S  E  M  N  M  D  Y  T

301 ATCACGATGTTTTTTCATCAGACTTGGAAAGATTCACGCTTAGCATACTATGAGACCACC  360
    I  T  M  F  F  H  Q  T  W  K  D  S  R  L  A  Y  Y  E  T  T

361 CTGAACTTGACCCTGGACTATCGGATGCATGAGAAGTTGTGGGTCCCTGACTGCTACTTT  420
    L  N  L  T  L  D  Y  R  M  H  E  K  L  W  V  P  D  C  Y  F

421 CTGAACAGCAAGGATGCTTTCGTGCATGATGTGACTGTGGAGAATCGCGTGTTTCAGCTT  480
    L  N  S  K  D  A  F  V  H  D  V  T  V  E  N  R  V  F  Q  L

481 CACCCAGATGGAACGGTGCGGTACGGCATCCGACTCACCACTACAGCAGTTTGTTCCCTG  540
    H  P  D  G  T  V  R  Y  G  I  R  L  T  T  T  A  V  C  S  L

541 GATCTGCATAAATTCCCTATGGACAAGCAGGCCTGCAACCTGGTGGTAGAGAGCTATGGT  600
    D  L  H  K  F  P  M  D  K  Q  A  C  N  L  V  V  E  S  Y  G

601 TACACGGTTGAAGACATCATATTATTCTGGGATGACAATGGGAACGCCATCCACATGACT  660
    Y  T  V  E  D  I  I  L  F  W  D  D  N  G  N  A  I  H  M  T

661 GAGGAGCTGCATATCCCTCAGTTCACTTTCCTGGGAAGGACGATTACTAGCAAGGAGGTG  720
    E  E  L  H  I  P  Q  F  T  F  L  G  R  T  I  T  S  K  E  V

721 TATTTCTACACAGGTTCCTACATACGCCTGATACTGAAGTTCCAGGTTCAGAGGGAAGTT  780
    Y  F  Y  T  G  S  Y  I  R  L  I  L  K  F  Q  V  Q  R  E  V

781 AACAGCTACCTTGTGCAAGTCTACTGGCCTACTGTCCTCACCACTATTACCTCTTGGATA  840
    N  S  Y  L  V  Q  V  Y  W  P  T  V  L  T  T  I  T  S  W  I

841 TCGTTTTGGATGAACTATGATTCCTCTGCAGCCAGGGTGACAATTGGCTTAACTTCAATG  900
    S  F  W  M  N  Y  D  S  S  A  A  R  V  T  I  G  L  T  S  M

901 CTCATCCTGACCACCATCGACTCACATCTGCGGGATAAGCTCCCCAACATTTCCTGTATC  960
    L  I  L  T  T  I  D  S  H  L  R  D  K  L  P  N  I  S  C  I

961 AAGGCCATTGATATCTATATCCTCGTGTGCTTGTTCTTTGTGTTCCTGTCCTTGCTGGAG 1020
    K  A  I  D  I  Y  I  L  V  C  L  F  F  V  F  L  S  L  L  E
```

FIG. 1A

```
1021 TATGTCTACATCAACTATCTTTTCTACAGTCGAGGACCTCGGCGCCAGCCTAGGCGACGC 1080
     Y V Y I N Y L F Y S R G P R R Q P R R R

1081 AGGAGACCCCGAAGAGTCATTGCCCGCTACCGCTACCAGCAAGTGGTGGTAGGAAACGTG 1140
     R R P R R V I A R Y R Y Q Q V V V G N V

1141 CAGGATGGCCTGATTAACGTGGAAGACGGAGTCAGCTCTCTCCCCATCACCCCAGCGCAG 1200
     Q D G L I N V E D G V S S L P I T P A Q

1201 GCCCCCCTGGCAAGCCCGGAAAGCCTCGGTTCTTTGACGTCCACCTCCGAGCAGGCCCAG 1260
     A P L A S P E S L G S L T S T S E Q A Q

1261 CTGGCCACCTCGGAAAGCCTCAGCCCACTCACTTCTCTCTCAGGCCAGGCCCCCCTGGCC 1320
     L A T S E S L S P L T S L S G Q A P L A

1321 ACTGGAGAAAGCCTGAGCGATCTCCCCTCCACCTCAGAGCAGGCCCGGCACAGCTATGGT 1380
     T G E S L S D L P S T S E Q A R H S Y G

1381 GTTCGCTTTAATGGTTTCCAGGCTGATGACAGTATTATTCCTACCGAAATCCGCAACCGT 1440
     V R F N G F Q A D D S I I P T E I R N R

1441 GTCGAAGCCCATGGCCATGGTGTTACCCATGACCATGAAGATTCCAATGAGAGCTTGAGC 1500
     V E A H G H G V T H D H E D S N E S L S

1501 TCGGATGAGCGCCATGGCCATGGCCCCAGTGGGAAGCCCATGCTTCACCATGGCGAGAAG 1560
     S D E R H G H G P S G K P M L H H G E K

1561 GGTGTGCAAGAAGCAGGCTGGGACCTTGATGACAACAATGACAAGAGCGACTGCCTTGCC 1620
     G V Q E A G W D L D D N N D K S D C L A

1621 ATTAAGGAGCAATTCAAGTGTGATACTAACAGTACCTGGGGCCTTAATGATGATGAGCTC 1680
     I K E Q F K C D T N S T W G L N D D E L

1681 GTGGCCCATGGCCAAGAGAAGGACAGTAGCTCAGAGTCTGAGGATAGTTGCCCCCCAAGC 1740
     V A H G Q E K D S S S E S E D S C P P S

1741 CCTGGGTGCTCCTTCACTGAAGGGTTCTCCTTCGATCTCTTTAATCCTGACTACGTCCCA 1800
     P G C S F T E G F S F D L F N P D Y V P

1801 AAGGTCGACAAGTGGTCCCGGTTCCTCTTCCCTCTGGCCTTTGGGTTGTTCAACATTGTT 1860
     K V D K W S R F L F P L A F G L F N I V

1861 TACTGGGTATACCATATGTATTAG 1884
     Y W V Y H M Y *
```

FIG.1B

Human θ Subunit

```
  1 ATGCTGCGAGCCGCAGTGATCCTGCTGCTCATCAGGACCTGGCTCGCGGAGGGCAACTAC   60
    M   L   R   A   A   V   I   L   L   L   I   R   T   W   L   A   E   G   N   Y

61 CCCAGTCCCATCCCGAAATTCCACTTCGAGTTCTCCTCTGCTGTGCCCGAAGTCGTCCTG  120
    P   S   P   I   P   K   F   H   F   E   F   S   S   A   V   P   E   V   V   L

121 AACCTCTTCAACTGCAAAAATTGTGCAAATGAAGCTGTGGTTCAAAAGATTTTGGACAGG  180
    N   L   F   N   C   K   N   C   A   N   E   A   V   V   Q   K   I   L   D   R

181 GTGCTGTCAAGATACGATGTCCGCCTGAGACCGAATTTTGGAGGTGCCCCTGTGCCTGTG  240
    V   L   S   R   Y   D   V   R   L   R   P   N   F   G   G   A   P   V   P   V

241 AGAATATCTATTTATGTCACGAGCATTGAACAGATCTCAGAAATGAATATGGACTACACG  300
    R   I   S   I   Y   V   T   S   I   E   Q   I   S   E   M   N   M   D   Y   T

301 ATCACGATGTTTTTTCATCAGACTTGGAAAGATTCACGCTTAGCATACTATGAGACCACC  360
    I   T   M   F   F   H   Q   T   W   K   D   S   R   L   A   Y   Y   E   T   T

361 CTGAACTTGACCCTGGACTATCGGATGCATGAGAAGTTGTGGGTCCCTGACTGCTACTTT  420
    L   N   L   T   L   D   Y   R   M   H   E   K   L   W   V   P   D   C   Y   F

421 TTGAACAGCAAGGATGCTTTCGTGCATGATGTGACTGTGGAGAATCGCGTGTTTCAGCTT  480
    L   N   S   K   D   A   F   V   H   D   V   T   V   E   N   R   V   F   Q   L

481 CACCCAGATGGAACGGTGCGGTACGGCATCCGACTCACCACTACAGCAGCTTGTTCCCTG  540
    H   P   D   G   T   V   R   Y   G   I   R   L   T   T   T   A   A   C   S   L

541 GATCTGCATAAATTCCCTATGGACAAGCAGGCCTGCAACCTGGTGGTAGAGAGCTATGGT  600
    D   L   H   K   F   P   M   D   K   Q   A   C   N   L   V   V   E   S   Y   G

601 TACACGGTTGAAGACATCATATTATTCTGGGATGACAATGGGAACGCCATCCACATGACT  660
    Y   T   V   E   D   I   I   L   F   W   D   D   N   G   N   A   I   H   M   T

661 GAGGAGCTGCATATCCCTCAGTTCACTTTCCTGGGAAGGACGATTACTAGCAAGGAGGTG  720
    E   E   L   H   I   P   Q   F   T   F   L   G   R   T   I   T   S   K   E   V

721 TATTTCTACACAGGTTCCTACATACGCCTGATACTGAAGTTCCAGGTTCAGAGGGAAGTT  780
    Y   F   Y   T   G   S   Y   I   R   L   I   L   K   F   Q   V   Q   R   E   V

781 AACAGCTACCTTGTGCAAGTCTACTGGCCTACTGTCCTCACCACTATTACCTCTTGGATA  840
    N   S   Y   L   V   Q   V   Y   W   P   T   V   L   T   T   I   T   S   W   I
```

FIG.2A

```
 841 TCGTTTTGGATGAACTATGATTCCTCTGCAGCCAGGGTGACAATTGGCTTAACTTCAATG  900
      S  F  W  M  N  Y  D  S  S  A  A  R  V  T  I  G  L  T  S  M

901 CTCATCCTGACCACCATCGACTCACATCTGCGGGATAAGCTCCCCAACATTTCCTGTATC  960
      L  I  L  T  T  I  D  S  H  L  R  D  K  L  P  N  I  S  C  I

961 AAGGCCATTGATATCTATATCCTCGTGTGCTTGTTCTTTGTGTTCCTGTCCTTGCTGGAG 1020
      K  A  I  D  I  Y  I  L  V  C  L  F  F  V  F  L  S  L  L  E

1021 TATGTCTACATCAACTATCTTTTCTACAGTCGAGGACCTCGGCGCCAGCCTAGGCGACAC 1080
      Y  V  Y  I  N  Y  L  F  Y  S  R  G  P  R  R  Q  P  R  R  H

1081 AGGAGACCCCGAAGAGTCATTGCCCGCTACCGCTACCAGCAAGTGGTGGTAGGAAACGTG 1140
      R  R  P  R  R  V  I  A  R  Y  R  Y  Q  Q  V  V  V  G  N  V

1141 CAGGATGGCCTGATTAACGTGGAAGACGGAGTCAGCTCTCTCCCCATCACCCCAGCGCAG 1200
      Q  D  G  L  I  N  V  E  D  G  V  S  S  L  P  I  T  P  A  Q

1201 GCCCCCCTGGCAAGCCCGGAAAGCCTCGGTTCTTTGACGTCCACCTCCGAGCAGGCCCAG 1260
      A  P  L  A  S  P  E  S  L  G  S  L  T  S  T  S  E  Q  A  Q

1261 CTGGCCACCTCGGAAAGCCTCAGCCCACTCACTTCTCTCTCAGGCCAGGCCCCCCTGGCC 1320
      L  A  T  S  E  S  L  S  P  L  T  S  L  S  G  Q  A  P  L  A

1321 ACTGGAGAAAGCCTGAGCGATCTCCCCTCCACCTCAGAGCAGGCCCGGCACAGCTATGGT 1380
      T  G  E  S  L  S  D  L  P  S  T  S  E  Q  A  R  H  S  Y  G

1381 GTTCGCTTTAATGGTTTCCAGGCTGATGACAGTATTTTTCCTACCGAAATCCGCAACCGT 1440
      V  R  F  N  G  F  Q  A  D  D  S  I  F  P  T  E  I  R  N  R

1441 GTCGAAGCCCATGGCCATGGTGTTACCCATGACCATGAAGATTCCAATGAGAGCTTGAGC 1500
      V  E  A  H  G  H  G  V  T  H  D  H  E  D  S  N  E  S  L  S

1501 TCGGATGAGCGCCATGGCCATGGCCCCAGTGGGAAGCCCATGCTTCACCATGGCGAGAAG 1560
      S  D  E  R  H  G  H  G  P  S  G  K  P  M  L  H  H  G  E  K

1561 GGTGTGCAAGAAGCAGGCTGGGACCTTGATGACAACAATGACAAGAGCGACTGCCTTGCC 1620
      G  V  Q  E  A  G  W  D  L  D  D  N  N  D  K  S  D  C  L  A

1621 ATTAAGGAGCAATTCAAGTGTGATACTAACAGTACCTGGGGCCTTAATGATGATGAGCTC 1680
      I  K  E  Q  F  K  C  D  T  N  S  T  W  G  L  N  D  D  E  L

1681 ATGGCCCATGGCCAAGAGAAGGACAGTAGCTCAGAGTCTGAGGATAGTTGCCCCCCAAGC 1740
      M  A  H  G  Q  E  K  D  S  S  S  E  S  E  D  S  C  P  P  S
```

FIG.2B

```
1741 CCTGGGTGCTCCTTCACTGAAGGGTTCTCCTTCGATCTCTTTAATCCTGACTACGTCCCA 1800
      P   G   C   S   F   T   E   G   F   S   F   D   L   F   N   P   D   Y   V   P

1801 AAGGTCGACAAGTGGTCCCGGTTCCTCTTCCCTCTGGCCTTTGGGTTGTTCAACATTGTT 1860
      K   V   D   K   W   S   R   F   L   F   P   L   A   F   G   L   F   N   I   V

1861 TACTGGGTATACCATATGTATTAG 1884
      Y   W   V   Y   H   M   Y   *
```

FIG.2C

SEQUENCE LISTING

<160> NUMBER OF SEQ ID NOS: 16

<210> SEQ ID NO 1
<211> LENGTH: 1884
<212> TYPE: DNA
<213> ORGANISM: Homo Sapien

<400> SEQUENCE: 1

```
atgctgcgag ccgcagtgat cctgctgctc atcaggacct ggctcgcgga gggcaactac      60
cccagtccca tcccgaaatt ccacttcgag ttctcctctg ctgtgcccga agtcgtcctg     120
aacctcttca actgcaaaaa ttgtgcaaat gaagctgtgg ttcaaaagat tttggacagg     180
```

-continued

```
gtgctgtcaa gatacgatgt ccgcctgaga ccgaattttg gaggtgcccc tgtgcctgtg    240
agaatatcta tttatgtcac gagcattgaa cagatctcag aaatgaatat ggactacacg    300
atcacgatgt tttttcatca gacttggaaa gattcacgct tagcatacta tgagaccacc    360
ctgaacttga ccctggacta tcggatgcat gagaagttgt gggtccctga ctgctacttt    420
ctgaacagca aggatgcttt cgtgcatgat gtgactgtgg agaatcgcgt gtttcagctt    480
cacccagatg aacggtgcg gtacggcatc cgactcacca ctacagcagt ttgttccctg    540
gatctgcata aattccctat ggacaagcag gcctgcaacc tggtggtaga gagctatggt    600
tacacggttg aagacatcat attattctgg gatgacaatg ggaacgccat ccacatgact    660
gaggagctgc atatccctca gttcactttc ctgggaagga cgattactag caaggaggtg    720
tatttctaca caggttccta catacgcctg atactgaagt tccaggttca gagggaagtt    780
aacagctacc ttgtgcaagt ctactggcct actgtcctca ccactattac ctcttggata    840 tcgtttttgga tgaactatga ttcctctgca gccagggtga caattggctt aacttcaatg    900
ctcatcctga ccaccatcga ctcacatctg cgggataagc tccccaacat ttcctgtatc    960
aaggccattg atatctatat cctcgtgtgc ttgttctttg tgttcctgtc cttgctggag   1020
tatgtctaca tcaactatct tttctacagt cgaggacctc ggcgccagcc taggcgacgc   1080
aggagacccc gaagagtcat tgcccgctac cgctaccagc aagtggtggt aggaaacgtg   1140
caggatggcc tgattaacgt ggaagacgga gtcagctctc tccccatcac ccagcgcag   1200 gccccctgg caagcccgga aagcctcggt tctttgacgt ccacctccga gcaggcccag   1260
ctggccacct cggaaagcct cagcccactc acttctctct caggccaggc cccctggcc   1320 actggagaaa gcctgagcga tctcccctcc acctcagagc aggcccggca cagctatggt   1380
gttcgcttta atggtttcca ggctgatgac agtattattc ctaccgaaat ccgcaaccgt   1440
gtcgaagccc atggccatgg tgttacccat gaccatgaag attccaatga gagcttgagc   1500
tcggatgagc gccatggcca tggccccagt gggaagccca tgcttcacca tggcgagaag   1560
ggtgtgcaag aagcaggctg ggaccttgat gacaacaatg acaagagcga ctgccttgcc   1620
attaaggagc aattcaagtg tgatactaac agtacctggg gccttaatga tgatgagctc   1680
gtggcccatg ccaagagaa ggacagtagc tcagagtctg aggatagttg ccccccaagc   1740
cctgggtgct ccttcactga agggttctcc ttcgatctct taatcctga ctacgtccca   1800 aaggtcgaca agtggtcccg gttcctcttc cctctggcct tgggttgtt caacattgtt   1860 tactgggtat accatatgta ttag                                         1884
```

<210> SEQ ID NO 2
<211> LENGTH: 627
<212> TYPE: PRT
<213> ORGANISM: Homo Sapien

<400> SEQUENCE: 2

```
Met Leu Arg Ala Ala Val Ile Leu Leu Leu Ile Arg Thr Trp Leu Ala
 1               5                   10                  15

Glu Gly Asn Tyr Pro Ser Pro Ile Pro Lys Phe His Phe Glu Phe Ser
                20                  25                  30

Ser Ala Val Pro Glu Val Val Leu Asn Leu Phe Asn Cys Lys Asn Cys
            35                  40                  45

Ala Asn Glu Ala Val Val Gln Lys Ile Leu Asp Arg Val Leu Ser Arg
        50                  55                  60
```

-continued

```
Tyr Asp Val Arg Leu Arg Pro Asn Phe Gly Gly Ala Pro Val Pro Val
 65                  70                  75                  80

Arg Ile Ser Ile Tyr Val Thr Ser Ile Glu Gln Ile Ser Glu Met Asn
                 85                  90                  95

Met Asp Tyr Thr Ile Thr Met Phe Phe His Gln Thr Trp Lys Asp Ser
            100                 105                 110

Arg Leu Ala Tyr Glu Thr Thr Leu Asn Leu Thr Leu Asp Tyr Arg
        115                 120                 125

Met His Glu Lys Leu Trp Val Pro Asp Cys Tyr Phe Leu Asn Ser Lys
    130                 135                 140

Asp Ala Phe Val His Asp Val Thr Val Glu Asn Arg Val Phe Gln Leu
145                 150                 155                 160

His Pro Asp Gly Thr Val Arg Tyr Gly Ile Arg Leu Thr Thr Thr Ala
                165                 170                 175

Val Cys Ser Leu Asp Leu His Lys Phe Pro Met Asp Lys Gln Ala Cys
            180                 185                 190

Asn Leu Val Val Glu Ser Tyr Gly Tyr Thr Val Glu Asp Ile Ile Leu
        195                 200                 205

Phe Trp Asp Asp Asn Gly Asn Ala Ile His Met Thr Glu Glu Leu His
    210                 215                 220

Ile Pro Gln Phe Thr Phe Leu Gly Arg Thr Ile Thr Ser Lys Glu Val
225                 230                 235                 240

Tyr Phe Tyr Thr Gly Ser Tyr Ile Arg Leu Ile Leu Lys Phe Gln Val
                245                 250                 255

Gln Arg Glu Val Asn Ser Tyr Leu Val Gln Val Tyr Trp Pro Thr Val
            260                 265                 270

Leu Thr Thr Ile Thr Ser Trp Ile Ser Phe Trp Met Asn Tyr Asp Ser
        275                 280                 285

Ser Ala Ala Arg Val Thr Ile Gly Leu Thr Ser Met Leu Ile Leu Thr
    290                 295                 300

Thr Ile Asp Ser His Leu Arg Asp Lys Leu Pro Asn Ile Ser Cys Ile
305                 310                 315                 320

Lys Ala Ile Asp Ile Tyr Ile Leu Val Cys Leu Phe Val Phe Leu
                325                 330                 335

Ser Leu Leu Glu Tyr Val Tyr Ile Asn Tyr Leu Phe Tyr Ser Arg Gly
            340                 345                 350

Pro Arg Arg Gln Pro Arg Arg Arg Arg Pro Arg Val Ile Ala
        355                 360                 365

Arg Tyr Arg Tyr Gln Gln Val Val Gly Asn Val Gln Asp Gly Leu
    370                 375                 380

Ile Asn Val Glu Asp Gly Val Ser Ser Leu Pro Ile Thr Pro Ala Gln
385                 390                 395                 400

Ala Pro Leu Ala Ser Pro Glu Ser Leu Gly Ser Leu Thr Ser Thr Ser
                405                 410                 415

Glu Gln Ala Gln Leu Ala Thr Ser Glu Ser Leu Ser Pro Leu Thr Ser
            420                 425                 430

Leu Ser Gly Gln Ala Pro Leu Ala Thr Gly Glu Ser Leu Ser Asp Leu
        435                 440                 445

Pro Ser Thr Ser Glu Gln Ala Arg His Ser Tyr Gly Val Arg Phe Asn
    450                 455                 460

Gly Phe Gln Ala Asp Asp Ser Ile Ile Pro Thr Glu Ile Arg Asn Arg
465                 470                 475                 480

Val Glu Ala His Gly His Gly Val Thr His Asp His Glu Asp Ser Asn
```

```
                        485                 490                     495
        Glu Ser Leu Ser Ser Asp Glu Arg His Gly His Gly Pro Ser Gly Lys
                        500                 505                 510
        Pro Met Leu His His Gly Glu Lys Gly Val Gln Glu Ala Gly Trp Asp
                        515                 520                 525
        Leu Asp Asp Asn Asn Asp Lys Ser Asp Cys Leu Ala Ile Lys Glu Gln
                        530                 535                 540
        Phe Lys Cys Asp Thr Asn Ser Thr Trp Gly Leu Asn Asp Asp Glu Leu
        545                 550                 555                 560
        Val Ala His Gly Gln Glu Lys Asp Ser Ser Glu Ser Glu Asp Ser
                        565                 570                 575
        Cys Pro Pro Ser Pro Gly Cys Ser Phe Thr Glu Gly Phe Ser Phe Asp
                        580                 585                 590
        Leu Phe Asn Pro Asp Tyr Val Pro Lys Val Asp Lys Trp Ser Arg Phe
                        595                 600                 605
        Leu Phe Pro Leu Ala Phe Gly Leu Phe Asn Ile Val Tyr Trp Val Tyr
                        610                 615                 620
        His Met Tyr
        625

<210> SEQ ID NO 3
<211> LENGTH: 1884
<212> TYPE: DNA
<213> ORGANISM: Homo Sapien

<400> SEQUENCE: 3
atgctgcgag ccgcagtgat cctgctgctc atcaggacct ggctcgcgga gggcaactac     60
cccagtccca tcccgaaatt ccacttcgag ttctcctctg ctgtgcccga agtcgtcctg    120
aacctcttca actgcaaaaa ttgtgcaaat gaagctgtgg ttcaaaagat tttggacagg    180
gtgctgtcaa gatacgatgt ccgcctgaga ccgaattttg gaggtgcccc tgtgcctgtg    240
agaatatcta tttatgtcac gagcattgaa cagatctcag aaatgaatat ggactacacg    300
atcacgatgt tttttcatca gacttggaaa gattcacgct tagcatacta tgagaccacc    360
ctgaacttga ccctggacta tcggatgcat gagaagttgt gggtccctga ctgctacttt    420
ttgaacagca aggatgcttt cgtgcatgat gtgactgtgg agaatcgcgt gtttcagctt    480
cacccagatg aacggtgcgg gtacggcatc cgactcacca ctacagcagc ttgttccctg    540
gatctgcata aattccctat ggacaagcag gcctgcaacc tggtggtaga gagctatggt    600
tacacggttg aagacatcat attattctgg gatgacaatg ggaacgccat ccacatgact    660
gaggagctgc atatccctca gttcactttc ctgggaagga cgattactag caaggaggtg    720
tatttctaca caggttccta catacgcctg atactgaagt tccaggttca gagggaagtt    780
aacagctacc ttgtgcaagt ctactggcct actgtcctca ccactattac ctcttggata    840
tcgttttgga tgaactatga ttcctctgca gccagggtga caattggctt aacttcaatg    900
ctcatcctga ccaccatcga ctcacatctg cgggataagc tccccaacat ttcctgtatc    960
aaggccattg atatctatat cctcgtgtgc ttgttctttg tgttcctgtc cttgctggag   1020
tatgtctaca tcaactatct tttctacagt cgaggacctc ggcgccagcc taggcgacac   1080
aggagacccc gaagagtcat tgcccgctac cgctaccagc aagtggtggt aggaaacgtg   1140
caggatggcc tgattaacgt ggaagacgga gtcagctctc tccccatcac ccagcgcgca   1200
gcccccctgg caagcccgga aagcctcggt tctttgacgt ccacctccga gcaggcccag   1260
```

-continued

```
ctggccacct cggaaagcct cagcccactc acttctctct caggccaggc cccctggcc    1320 actggagaaa gcctgagcga tctcccctcc acctcagagc aggcccggca cagctatggt    1380
gttcgcttta atggtttcca ggctgatgac agtatttttc ctaccgaaat ccgcaaccgt    1440
gtcgaagccc atggccatgg tgttacccat gaccatgaag attccaatga gagcttgagc    1500
tcggatgagc gccatggcca tggccccagt gggaagccca tgcttcacca tggcgagaag    1560
ggtgtgcaag aagcaggctg ggaccttgat gacaacaatg acaagagcga ctgccttgcc    1620
attaaggagc aattcaagtg tgatactaac agtacctggg gccttaatga tgatgagctc    1680
atggcccatg ccaagagaa ggacagtagc tcagagtctg aggatagttg cccccccaagc    1740 cctgggtgct ccttcactga agggttctcc ttcgatctct ttaatcctga ctacgtccca    1800
aaggtcgaca agtggtcccg gttcctcttc cctctggcct ttgggttgtt caacattgtt    1860
tactgggtat accatatgta ttag                                           1884
```

<210> SEQ ID NO 4
<211> LENGTH: 627
<212> TYPE: PRT
<213> ORGANISM: Homo Sapien

<400> SEQUENCE: 4

```
Met Leu Arg Ala Ala Val Ile Leu Leu Ile Arg Thr Trp Leu Ala
 1               5                  10                  15

Glu Gly Asn Tyr Pro Ser Pro Ile Pro Lys Phe His Phe Glu Phe Ser
                20                  25                  30

Ser Ala Val Pro Glu Val Val Leu Asn Leu Phe Asn Cys Lys Asn Cys
            35                  40                  45

Ala Asn Glu Ala Val Val Gln Lys Ile Leu Asp Arg Val Leu Ser Arg
        50                  55                  60

Tyr Asp Val Arg Leu Arg Pro Asn Phe Gly Gly Ala Pro Val Pro Val
    65                  70                  75                  80

Arg Ile Ser Ile Tyr Val Thr Ser Ile Glu Gln Ile Ser Glu Met Asn
                85                  90                  95

Met Asp Tyr Thr Ile Thr Met Phe Phe His Gln Thr Trp Lys Asp Ser
               100                 105                 110

Arg Leu Ala Tyr Tyr Glu Thr Thr Leu Asn Leu Thr Leu Asp Tyr Arg
           115                 120                 125

Met His Glu Lys Leu Trp Val Pro Asp Cys Tyr Phe Leu Asn Ser Lys
       130                 135                 140

Asp Ala Phe Val His Asp Val Thr Val Glu Asn Arg Val Phe Gln Leu
145                 150                 155                 160

His Pro Asp Gly Thr Val Arg Tyr Gly Ile Arg Leu Thr Thr Thr Ala
                165                 170                 175

Ala Cys Ser Leu Asp Leu His Lys Phe Pro Met Asp Lys Gln Ala Cys
            180                 185                 190

Asn Leu Val Val Glu Ser Tyr Gly Tyr Thr Val Glu Asp Ile Ile Leu
        195                 200                 205

Phe Trp Asp Asp Asn Gly Asn Ala Ile His Met Thr Glu Glu Leu His
    210                 215                 220

Ile Pro Gln Phe Thr Phe Leu Gly Arg Thr Ile Thr Ser Lys Glu Val
225                 230                 235                 240

Tyr Phe Tyr Thr Gly Ser Tyr Ile Arg Leu Ile Leu Lys Phe Gln Val
                245                 250                 255

Gln Arg Glu Val Asn Ser Tyr Leu Val Gln Val Tyr Trp Pro Thr Val
```

-continued

```
                    260                 265                 270
Leu Thr Thr Ile Thr Ser Trp Ile Ser Phe Trp Met Asn Tyr Asp Ser
            275                 280                 285

Ser Ala Ala Arg Val Thr Ile Gly Leu Thr Ser Met Leu Ile Leu Thr
            290                 295                 300

Thr Ile Asp Ser His Leu Arg Asp Lys Leu Pro Asn Ile Ser Cys Ile
305                 310                 315                 320

Lys Ala Ile Asp Ile Tyr Ile Leu Val Cys Leu Phe Val Phe Leu
                325                 330                 335

Ser Leu Leu Glu Tyr Val Tyr Ile Asn Tyr Leu Phe Tyr Ser Arg Gly
            340                 345                 350

Pro Arg Arg Gln Pro Arg Arg His Arg Arg Pro Arg Val Ile Ala
            355                 360                 365

Arg Tyr Arg Tyr Gln Gln Val Val Gly Asn Val Gln Asp Gly Leu
370                 375                 380

Ile Asn Val Glu Asp Gly Val Ser Ser Leu Pro Ile Thr Pro Ala Gln
385                 390                 395                 400

Ala Pro Leu Ala Ser Pro Glu Ser Leu Gly Ser Leu Thr Ser Thr Ser
            405                 410                 415

Glu Gln Ala Gln Leu Ala Thr Ser Glu Ser Leu Ser Pro Leu Thr Ser
            420                 425                 430

Leu Ser Gly Gln Ala Pro Leu Ala Thr Gly Glu Ser Leu Ser Asp Leu
            435                 440                 445

Pro Ser Thr Ser Glu Gln Ala Arg His Ser Tyr Gly Val Arg Phe Asn
            450                 455                 460

Gly Phe Gln Ala Asp Ser Ile Phe Pro Thr Glu Ile Arg Asn Arg
465                 470                 475                 480

Val Glu Ala His Gly His Gly Val Thr His Asp His Glu Asp Ser Asn
                485                 490                 495

Glu Ser Leu Ser Ser Asp Glu Arg His Gly His Gly Pro Ser Gly Lys
            500                 505                 510

Pro Met Leu His His Gly Glu Lys Gly Val Gln Glu Ala Gly Trp Asp
            515                 520                 525

Leu Asp Asp Asn Asn Asp Lys Ser Asp Cys Leu Ala Ile Lys Glu Gln
530                 535                 540

Phe Lys Cys Asp Thr Asn Ser Thr Trp Gly Leu Asn Asp Asp Glu Leu
545                 550                 555                 560

Met Ala His Gly Gln Glu Lys Asp Ser Ser Ser Glu Ser Glu Asp Ser
                565                 570                 575

Cys Pro Pro Ser Pro Gly Cys Ser Phe Thr Glu Gly Phe Ser Phe Asp
            580                 585                 590

Leu Phe Asn Pro Asp Tyr Val Pro Lys Val Asp Lys Trp Ser Arg Phe
            595                 600                 605

Leu Phe Pro Leu Ala Phe Gly Leu Phe Asn Ile Val Tyr Trp Val Tyr
            610                 615                 620

His Met Tyr
625

<210> SEQ ID NO 5
<211> LENGTH: 19
<212> TYPE: DNA
<213> ORGANISM: Homo Sapien

<400> SEQUENCE: 5
```

-continued gcaaatgaag ctgtggttc                                          19

<210> SEQ ID NO 6
<211> LENGTH: 20
<212> TYPE: DNA
<213> ORGANISM: Homo Sapien

<400> SEQUENCE: 6
caatgttgaa caacccaaag                                         20

<210> SEQ ID NO 7
<211> LENGTH: 19
<212> TYPE: DNA
<213> ORGANISM: Homo Sapien

<400> SEQUENCE: 7
gcctgagacc gaattttgg                                          19

<210> SEQ ID NO 8
<211> LENGTH: 19
<212> TYPE: DNA
<213> ORGANISM: Homo Sapien

<400> SEQUENCE: 8
ggaaccggga ccacttgtc                                          19

<210> SEQ ID NO 9
<211> LENGTH: 18
<212> TYPE: DNA
<213> ORGANISM: Homo Sapien

<400> SEQUENCE: 9
tagtccaggg tcaagttc                                           18

<210> SEQ ID NO 10
<211> LENGTH: 20
<212> TYPE: DNA
<213> ORGANISM: Homo Sapien

<400> SEQUENCE: 10
tagtatgcta agcgtgaatc                                         20

<210> SEQ ID NO 11
<211> LENGTH: 18
<212> TYPE: DNA
<213> ORGANISM: Homo Sapien

<400> SEQUENCE: 11
gagtttgagg atagttgc                                           18

<210> SEQ ID NO 12
<211> LENGTH: 18
<212> TYPE: DNA
<213> ORGANISM: Homo Sapien

<400> SEQUENCE: 12
tgctccttca ctgaaggg                                           18

<210> SEQ ID NO 13
<211> LENGTH: 42
<212> TYPE: DNA
<213> ORGANISM: Homo Sapien

<400> SEQUENCE: 13

-continued

```
ccatgactca agcttgccac catgctgcga gccgcagtga tc                    42

<210> SEQ ID NO 14
<211> LENGTH: 27
<212> TYPE: DNA
<213> ORGANISM: Homo Sapien

<400> SEQUENCE: 14
tgaaaggagc acagcacagt gctcccg                                     27

<210> SEQ ID NO 15
<211> LENGTH: 45
<212> TYPE: DNA
<213> ORGANISM: Homo Sapien

<400> SEQUENCE: 15
ctgcttcttg cacacccttc tcgccatggt gaagcatggg cttcc                 45

<210> SEQ ID NO 16
<211> LENGTH: 45
<212> TYPE: DNA
<213> ORGANISM: Homo Sapien

<400> SEQUENCE: 16
tgtcgcctag gctggcgccg aggtcctcga ctgtagaaaa gatag                 45
```

HUMAN THETA SUBUNIT OF THE GABA$_A$ RECEPTOR

This specification claims the benefit of PCT/GB/01206, filed Apr. 24, 1998, and GB Application 9708479.2, filed Apr. 25, 1997.

This invention concerns the cloning of a novel cDNA sequence encoding a particular subunit of the human GABA$_A$ receptor. In addition, the invention relates to a stable cell line capable of expressing said cDNA and to the use of the cell line in a screening technique for the design and development of subtype-specific medicaments.

Gamma-amino butyric acid (GABA) is a major inhibitory neurotransmitter in the central nervous system. It mediates fast synaptic inhibition by opening the chloride channel intrinsic to the GABA$_A$ receptor. This receptor comprises a multimeric protein of molecular size 230–270 kDa with specific binding sites for a variety of drugs including benzodiazepines, barbiturates and β-carbolines, in addition to sites for the agonist ligand GABA (for reviews see MacDonald and Olsen, *Ann. Rev. Neurosci.*, 1994, 17, 569; and Whiting et al, *Int. Rev. Neurobiol.*, 1995, 38, 95).

Molecular biological studies demonstrate that the receptor is composed of several distinct types of subunit, which are divided into four classes (α, β, γ and δ) based on their sequence similarities. To date, in mammals, six types of α (Schofield et al., *Nature* (London), 1987, 328, 221; Levitan et al., *Nature* (London), 1988, 335, 76; Ymer et al., *EMBO J.*, 1989, 8, 1665; Pritchett & Seeberg, *J. Neurochem.*, 1990, 54, 802; Luddens et al., *Nature* (London), 1990, 346, 648; and Khrestchatisky et al., *Neuron*, 1989, 3, 745), three types of β (Ymer et al., *EMBO J.*, 1989, 8, 1665), three types of γ (Ymer et al., *EMBO J.*, 1990, 9, 3261; Shivers et al., *Neuron*, 1989, 3, 327: and Knoflach et al, *FEBS Lett.*, 1991, 293, 191) and one δ subunit (Shivers et al., *Neuron*, 1989, 3, 327) have been identified. More recently, a further member of the GABA receptor gene family, ε, has been identified (Davies et al, *Nature*, 1997, 385, 820). The polypeptide is 506 amino acids in length and exhibits greatest amino acid sequence identity with the GABA$_A$ receptor γ$_3$ subunit (47%), although this degree of homology is not sufficient for it to be classified as a fourth γ subunit.

The differential distribution of many of the subunits has been characterised by in situ hybridisation (Shivers et al., *Neuron*, 1989, 3, 327; Wisden et al, *J. Neurosci.*, 1992, 12, 1040; and Laurie et al, *J. Neurosci*, 1992, 12, 1063) and this has permitted it to be speculated which subunits, by their co-localisation, could theoretically exist in the same receptor complex.

Various combinations of subunits have been co-transfected into cells to identify synthetic combinations of subunits whose pharmacology parallels that of bona fide GABA$_A$ receptors in vivo (Pritchett et al., *Science*, 1989, 245, 1389; Pritchett and Seeberg, *J. Neurochem.*, 1990, 54, 1802; Luddens et al., *Nature* (London), 1990, 346, 648; Hadingham et al, *Mol. Pharmacol.*, 1993, 43, 970; and Hadingham et al., *Mol. Pharmacol.*, 1993, 44, 1211). This approach has revealed that, in addition to an α and β subunit, either γ$_1$ or γ$_2$ (Pritchett et al., *Nature* (London), 1989, 338, 582; Ymer et al., *EMBO J.*, 1990, 9, 3261; and Wafford et al., *Mol. Pharmacol.*, 1993, 44, 437) or γ$_3$ (Herb et al., *Proc. Natl. Acad. Sci. USA*, 1992, 89, 1433; Knoflach et al., *FEBS Lett.*, 1991, 293, 191; and Wilson-Shaw et al., *FEBS Lett.*, 1991, 284, 211) is also generally required to confer benzodiazepine sensitivity, and that the benzodiazepine pharmacology of the expressed receptor is largely dependent on the identity of the α and γ subunits present. Receptors containing a δ subunit (i.e. αγδ) do not appear to bind benzodiazepines (Shivers et al., *Neuron*, 1989, 3, 327; and Quirk et al., *J. Biol. Chem.*, 1994, 269, 16020). Combinations of subunits have been identified which exhibit the pharmacological profile of a BZ$_1$ type receptor (α$_1$β$_1$γ$_2$) and a BZ$_2$ type receptor (α$_2$β$_1$γ$_2$ or α$_3$β$_1$γ$_2$, Pritchett et al., *Nature* (London), 1989, 338, 582), as well as GABA$_A$ receptors with a novel pharmacology, α$_5$β$_2$γ$_2$ (Pritchett and Seeberg, *J. Neurochem.*, 1990, 54, 1802), α$_4$β$_2$γ$_2$ (Wisden et al, *FEBS Lett.*, 1991, 289, 227) and α$_6$β$_2$γ$_2$ (Luddens et al., *Nature* (London), 1990, 346, 648). The pharmacology of these expressed receptors appears similar to that of those identified in brain tissue by radioligand binding, and biochemical expperiments have begun to determine the subunit composition of native GABA receptors (McKernan & Whiting, *Tr. Neurosci.*, 1996, 19, 139). The exact structure of receptors in vivo has yet to be definitively elucidated.

The present invention relates to a new class of GABA receptor subunit, hereinafter referred to as the theta subunit (θ subunit).

The nucleotide sequence for the theta subunit, together with its deduced amino acid sequence corresponding thereto, is depicted in FIG. 1 of the accompanying drawings.

The present invention accordingly provides, in a first aspect, a DNA molecule encoding the theta subunit of the human GABA receptor comprising all or a portion of the sequence depicted in FIG. 1, or a modified human sequence.

In an alternative aspect, the present invention provides a DNA molecule encoding the theta subunit of the human GABA receptor comprising all or a portion of the sequence depicted in FIG. 2, or a modified human sequence.

The term "modified human sequence" as used herein referes to a variant of the DNA sequences depicted in FIG. 1 and FIG. 2. Such variants may be naturally occuring allelic variants or non-naturally occuring or "engineered" variants. Allelic variation is well known in the art in which the nucleotide sequence may have a substitution, deletion or addition of one or more nucleotides without substantial alteration of the function of the encoded polypeptide. Particularly preferred allelic variants arise from nucleotide substitution based on the degeneracy of the genetic code.

The sequencing of the novel cDNA molecules in accordance with the invention can conveniently be carried out by the standard procedure described in accompanying Example 1; or may be accomplished by alternative molecular cloning techniques which are well known in the art, such as those described by Maniatis et al. in *Molecular Cloning, A Laboratory Manual*, Cold Spring Harbor Press, New York, 2nd edition, 1989.

In a further aspect, the present invention also relates to polynucleotides (for example, cDNA, genomic DNA or synthetic DNA) which hybridize under stringent conditions to the DNA molecules depicted in FIG. 1 and FIG. 2. As used herein, the term "stringent conditions" will be understood to require at least 95% and preferably at least 97% identity between the hybridized sequences. Polynucleotides which hybridize under stringent conditions to the DNA molecules depicted in FIG. 1 and FIG. 2 preferably encode polypeptides which exhibit substantially the same biological activity or function as the polypeptides depicted in FIG. 1 and FIG. 2, respectively.

The present invention further relates to a GABA theta subunit polypeptide which has the deduced amino acid sequence of FIG. 1 or FIG. 2, as well as fragments, analogs and derivatives thereof.

The terms "fragment", "derivative" and "analog" when referring to the polypeptide of FIG. 1 or FIG. 2, means a polypeptide which retains essentially the same biological activity or function as the polypeptide depicted in FIG. 1 or FIG. 2. Thus, an analog may be, for example, a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or FIG. 2 may be one in which one or more of the amino acid residues are substituted with a conserved or non-conserved amino acid residue (preferably a conserved amino acid residue) and such substituted amino acid residues may or may not be one encoded by the genetic code; or one in which one or more of the amino acid residues includes a substituent group; or one in which the mature polypeptide is fused with another compound, such as a compound to increase the half-life of the polypeptide (for example, polyethylene glycol); or one in which the additional amino acids are fused to the mature polypeptide, such as a leader or secretory sequence or a sequence which is employed for purification of the mature polypeptide or a proprotein sequence. Such fragments, derivatives and analogs are deemed to be within the technical capabilities of those skilled in the art.

The polypeptides and DNA molecules of the present invention are preferably provided in an isolated form, and preferably are purified to homogeneity.

The term "isolated" means that the material is removed from its original environment (e.g., the natural environment if it is naturally occurring). For example, a naturally-occurring DNA molecule or polypeptide present in a living animal is not isolated, but the same DNA molecule or polypeptide, separated from some or all of the coexisting materials in the natural system, is isolated. Such DNA molecules could be part of a vector and/or such DNA molecules or polypeptides could be part of a composition, and still be isolated in that such vector or composition is not part of its natural environment.

In another aspect, the invention provides a recombinant expression vector comprising the nucleotide sequence of the human GABA receptor theta subunit together with additional sequences capable of directing the synthesis of the said human GABA receptor theta subunit in cultures of stably co-transfected eukaryotic cells.

The term "expression vectors" as used herein refers to DNA sequences that are required for the transcription of cloned copies of recombinant DNA sequences or genes and the translation of their mRNAs in an appropriate host. Such vectors can be used to express eukaryotic genes in a variety of hosts such as bacteria, blue-green algae, yeast cells, insect cells, plant cells and animal cells. Specifically designed vectors allow the shuttling of DNA between bacteria-yeast, bacteria-plant or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The term "cloning vector" as used herein refers to a DNA molecule, usually a small plasmid or bacteriophage DNA capable of self-replication in a host organism, and used to introduce a fragment of foreign DNA into a host cell. The foreign DNA combined with the vector DNA constitutes a recombinant DNA molecule which is derived from recombinant technology. Cloning vectors may include plasmids, bacteriophages, viruses and cosmids.

The recombinant expression vector in accordance with the invention may be prepared by inserting the nucleotide sequence of the GABA theta subunit into a suitable precursor expression vector (hereinafter referred to as the "precursor vector") using conventional recombinant DNA methodology known from the art. The precursor vector may be obtained commercially, or constructed by standard techniques from known expression vectors. The precursor vector suitably contains a selection marker, typically an antibiotic resistance gene, such as the neomycin or ampicillin resistance gene. The precursor vector preferably contains a neomycin resistance gene, adjacent the SV40 early splicing and polyadenylation region; an ampicillin resistance gene; and an origin of replication, e.g. pBR322 ori. The vector also preferably contains an inducible promoter, such as MMTV-LTR (inducible with dexamethasone) or metallothionin (inducible with zinc), so that transcription can be controlled in the cell line of this invention. This reduces or avoids any problem of toxicity in the cells because of the chloride channel intrinsic to the $GABA_A$ receptor.

One suitable precursor vector is pMAMneo, available from Clontech Laboratories Inc. (Lee et al., *Nature*, 1981, 294, 228; and Sardet et al., *Cell*, 1989, 56, 271). Alternatively the precursor vector pMSGneo can be constructed from the vectors pMSG and pSV2neo.

The recombinant expression vector of the present invention is then produced by cloning the GABA receptor theta subunit cDNA into the above precursor vector. The receptor subunit cDNA is subcloned from the vector in which it is harboured, and ligated into a restriction enzyme site, e.g. the Hind III site, in the polylinker of the precursor vector, for example pMAMneo or pMSGneo, by standard cloning methodology known from the art, and in particular by techniques analogous to those described herein. Before this subdoning, it is often advantageous, in order to improve expression, to modify the end of the theta subunit cDNA with additional 5' untranslated sequences, for example by modifying the 5' end of the theta subunit DNA by addition of 5' untranslated region sequences from the $\alpha_1$ subunit DNA. Alternatively, expression of the theta subunit cDNA may be modified by the insertion of an epitope tag sequence such as c-myc.

According to a further aspect of the present invention, there is provided a stably co-transfected eukaryotic cell line capable of expressing a GABA receptor, which receptor comprises the theta receptor subunit, at least one alpha receptor subunit and optionally one or more beta, gamma, delta, or epsilon receptor subunit.

This is achieved by co-transfecting cells with multiple expression vectors, each harbouring cDNAs encoding for an $\alpha$, $\theta$, and optionally one or more $\beta$, $\gamma$, $\delta$, or GABA receptor subunits. In a further aspect, therefore, the present invention provides a process for the preparation of a eukaryotic cell line capable of expressing a GABA receptor, which comprises stably co-transfecting a eukaryotic host cell with at least two expression vectors, one such vector harbouring the cDNA sequence encoding the theta GABA receptor subunit, and another such vector harbouring the cDNA sequence encoding an alpha GABA receptor subunit. The stable cell-line which is established expresses an $\alpha\theta$ GABA receptor.

Each receptor thereby expressed, comprising a unique combination of $\alpha$, $\theta$ and optionally one or more subunits selected from β, γ, δ or δ subunits, will be referred to hereinafter as a GABA receptor "subunit combination".

Expression of the GABA receptor may be accomplished by a variety of different promoter-expression systems in a variety of different host cells. The eukaryotic host cells suitably include yeast, insect and mammalian cells. Preferably the eukaryotic cells which can provide the host for the expression of the receptor are mammalian cells. Suitable host cells include rodent fibroblast lines, for example mouse Ltk⁻, Chinese hamster ovary (CHO) and baby hamster kidney (BHK); HeLa; and HEK293 cells. It is necessary to incorporate at least one α subunit, the θ subunit, and optionally one or more subunits selected from β, γδ or δ into the cell line in order to produce the required receptor. Within this limitation, the choice of receptor subunit combination is made according to the type of activity or selectivity which is being screened for.

In order to employ this invention most effectively for screening purposes, it is preferable to build up a library of cell lines, each with a different combination of subunits. Typically a library of 5 or 6 cell line types is convenient for this purpose. Preferred subunit combinations include: $\alpha\theta\beta$, $\alpha\theta\gamma$, $\alpha\theta\delta$, and $\alpha\theta\epsilon$, and most especially $\alpha_1\theta\gamma_2$. Further preferred subunit combinations include $\alpha\beta\theta\gamma$ and $\alpha\beta\theta\epsilon$, and most especially $\alpha_2\beta_1\theta\gamma_1$ and $\alpha_2\beta_3\theta\gamma_2$.

Cells are then co-transfected with the desired combination of the expression vectors. There are several commonly used techniques for transfection of eukaryotic cells in vitro. Calcium phosphate precipitation of DNA is most commonly used (Bachetti et al., *Proc. Natl. Acad. Sci. USA*, 1977, 74, 1590–1594; Maitland et al., *Cell*, 1977, 14, 133–141), and represents a favoured technique in the context of the present invention.

A small percentage of the host cells takes up the recombinant DNA. In a small percentage of those, the DNA will integrate into the host cell chromosome. Because an antibitotic resistance marker gene, such as the neomycin or zeocin resistance gene, will have been incorporated into these host cells, they can be selected by isolating the individual clones which will grow in the presence of the chosen antibiotic, e.g. neomycin or zeocin. Each such clone may then tested to identify those which will produce the receptor. This may be achieved by inducing the production, for example with dexamethasone, and then detecting the presence of receptor by means of radioligand binding.

Alternatively, expression of the GABA receptor may be effected in Xenopus oocytes (see, for instance, Hadingham et al. *Mol. Pharmacol.*, 1993, 44, 1211–1218). Briefly, isolated oocyte nuclei are injected directly with injection buffer or sterile water containing at least one alpha subunit, the theta subunit, and optionally one or more beta, gamma, delta or epsilon receptor subunits, engineered into a suitable expression vector. The oocytes are then incubated.

The expression of subunit combinations in the transfected oocytes may be demonstrated using conventional patch clamp assay. This assay measures the charge flow into and out of an electrode sealed on the surface of the cell. The flow of chloride ions entering the cell via the GABA gated ion channel is measured as a function of the current that leaves the cell to maintain electrical equilibrium within the cell as the gate opens.

In a further aspect, the present invention provides protein preparations of GABA receptor subunit combinations, especially human GABA receptor subunit combinations, derived from cultures of stably transfected eukaryotic cells.

The protein preparations of GABA receptor subunit combinations can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The GABA theta subunit polypeptide of the present invention is also useful for identifying other subunits of the GABA receptor. An example of a procedure for identifying these subunits comprises raising high titre polyclonal antisera against unique, bacterially expressed GABA theta polypeptides. These polyclonal antisera are then used to immunoprecipitate detergent-solubilized GABA receptors from a mammalian brain, for example, a rat brain.

The invention also provides preparations of membranes containing subunit combinations of the GABA receptor, especially human GABA receptor subunit combinations, derived from cultures of stably transfected eukaryotic cells.

The cell line, and the membrane preparations therefrom, according to the present invention have utility in screening and design of drugs which act upon the GABA receptor, for example benzodiazepines, barbiturates, β-carbolines and neurosteroids.

Receptor localisation studies using in situ hybridization in monkey brains shows that the θ subunit has a restricted localisation; residing mainly in components of the limbic system (involved in emotions such as rage, fear, motivation sexual behaviours and feeding); medial septum, cingulate cortex, the amygdala and hippocampal fields, in various hypothalamic nuclei, and in regions that have been associated with pain perception; the cingulate cortex, insular cortex, and in mid brain and pons structures.

The present invention accordingly provides the use of stably cotransfected cell lines described above, and membrane preparations derived therefrom, in screening for and designing medicaments which act upon GABA receptors comprising the θ subunit. Of particular interest in this context are molecules capable of interacting selectively with GABA receptors made up of varying subunit combinations. As will be readily apparent, the cell line in accordance with the present invention, and the membrane preparations derived therefrom, provide ideal systems for the study of structure, pharmacology and function of the various GABA receptor subtypes. In particular, preferred screens are functional assays utilizing the pharmacological properties of the GABA receptor subunit combinations of the present invention.

Thus, according to a further aspect of the present invention, there is provided a method for determining whether a ligand, not known to be capable of binding to a human $GABA_A$ receptor comprising the theta subunit, can bind to a human $GABA_A$ receptor comprising the theta subunit, which comprises contacting a mammalian cell comprising DNA molecules encoding at least one alpha receptor subunit, the theta receptor subunit, and optionally one or more beta, gamma, delta or epsilon receptor subunits with the ligand under conditions permitting binding of ligands known to bind to the $GABA_A$ receptor, detecting the presence of any of the ligand bound to the $GABA_A$ receptor comprising the theta subunit, and thereby determining whether the ligand binds to the $GABA_A$ receptor comprising the theta subunit. The theta subunit-encoding DNA in the cell may have a coding sequence substantially the same as the coding sequence shown in FIG. 1 or FIG. 2. Preferably, the mammalian cell is non-neuronal in origin. An example of a non-neuronal mammalian cell is a fibroblast cell such as an Ltk$^-$cell. The preferred method for determining whether a ligand is capable of binding to a human $GABA_A$ receptor comprising the theta subunit comprises contacting a transfected non-neuronal mammalian cell (i.e. a cell that does not naturally express any type of $GABA_A$ receptor, and thus will only express such a receptor if it is transfected into the cell) expressing a $GABA_A$ receptor comprising the theta subunit on its surface, or contacting a membrane preparation from such a transfected cell, with the ligand under conditions which are known to prevail, and thus to be associated with, in vivo binding of the ligands to a $GABA_A$ receptor comprising the theta subunit, detecting the presence of any of the ligand being tested bound to the $GABA_A$ receptor comprising the theta subunit on the surface of the cell, and thereby determining whether the ligand binds to a human $GABA_A$ receptor comprising the theta subunit. This response system may be based on ion flux changes measured, for example, by scintillation counting (where the ion is radiolabelled) or by interaction of the ion with a fluorescent marker. Particularly suitable ions are chloride ions. Such a host system is conveniently isolated from pre-existing cell lines. Such a transfection system provides a complete response system for investigation or assay of the activity of human $GABA_A$ receptors comprising the theta subunit with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. A transfection system constitutes a "drug discovery system" useful for the identification of natural or synthetic compounds with potential for drug development that can be further modified or used directly as therapeutic compounds to activate, inhibit or modulate the natural functions of human $GABA_A$ receptors comprising the theta subunit. The transfection system is also useful for determining the affinity and efficacy of known drugs at human $GABA_A$ receptor sites comprising the theta subunit.

This invention also provides a method of screening drugs to identify drugs which specifically interact with, and bind to, a human $GABA_A$ receptor comprising the theta subunit on the surface of a cell which comprises contacting a mammalian cell comprising DNA molecules encoding at least one alpha receptor subunit, the theta receptor subunit and optionally one or more beta, gamma, delta or epsilon receptor subunits on the surface of a cell with a plurality of drugs, determining those drugs which bind to the mammalian cell, and thereby identifying drugs which specifically interact with, and bind to, human $GABA_A$ receptors comprising the theta subunit. The theta subunit-encoding DNA in the cell may have a coding sequence substantially the same as the coding sequence shown in FIG. 1 or FIG. 2. Preferably, the mammalian cell is non-neuronal in origin. An example of a non-neuronal mammalian cell is a fibroblast cell such as an Ltk$^-$cell. Drug candidates are identified by choosing chemical compounds which bind with high affinity to the expressed $GABA_A$ receptor protein in transfected cells, using radioligand binding methods well known in the art. Drug candidates are also screened for selectivity by identifying compounds which bind with high affinity to one particular $GABA_A$ receptor combination but do not bind with high affinity to any other $GABA_A$ receptor combination or to any other known receptor site. Because selective, high affinity compounds interact primarily with the target $GABA_A$ receptor site after administration to the patient, the chances of producing a drug with unwanted side effects are minimized by this approach.

In the above screens, the mammalian cell may, for example, comprise DNA molecules encoding at least one alpha receptor subunit, the theta subunit, and optionally one or more gamma receptor subunits and optionally one or more beta receptor subunits.

More preferably, in the above screens, the mammalian cell comprises DNA molecules encoding at least one alpha receptor subunit, at least one gamma receptor subunit and the theta receptor subunit.

Ligands or drug candidates identified above may be agonists or antagonists at human $GABA_A$ receptors comprising the theta subunit, or may be agents which allosterically modulate a human $GABA_A$ receptor comprising the theta subunit. These ligands or drug candidates identified above may be employed as therapeutic agents, for example, for the modulation of emotions such as rage and fear, of sexual and appetite behaviours and of pain perception.

The ligands or drug candidates of the present invention thus identified as therapeutic agents may be employed in combination with a suitable pharmaceutical carrier. Such compositions comprise a therapeutically effective amount of the agonist or antagonist, and a pharmaceutically acceptable carrier or excipient.

Preferably the compositions containing the ligand or drug candidate identified according to the methods of the present invention are in unit dosage forms such as tablets, pills, capsules, wafers and the like. Additionally, the therapeutic agent may be presented as granules or powders for extemporaneous formulation as volume defined solutions or suspensions. Alternatively, the therapeutic agent may be presented in ready-prepared volume defined solutions or suspensions. Preferred forms are tablets and capsules.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions of the present invention may also be administered via the buccal cavity using conventional technology, for example, absorption wafers.

Compositions in the form of tablets, pills, capsules or wafers for oral administration are particularly preferred.

A minimum dosage level for the ligand or drug candidate identified according to the methods of the present invention is about 0.05 mg per day, preferably about 0.5 mg per day and especially about 2.5 mg per day. A maximum dosage level for the ligand or drug candidate is about 3000 mg per day, preferably about 1500 mg per day and especially about 500 mg per day. The compounds are administered on a regimen of 1 to 4 times daily, preferably once or twice daily, and especially once a day.

It will be appreciated that the amount of the therapeutic agent required for use therapy will vary not only with the particular compounds or compositions selected but also with the route of administration, the nature of the condition being treated, and the age and condition of the patient, and will ultimately be at the discretion of the patient's physician or pharmacist.

DESCRIPTION OF FIGURES

FIG. 1: Nucleotide sequence for the theta subunit, together with its deduced amino acid sequence corresponding thereto (SEQ.ID.NO.1 and SEQ.ID.NO.2, respectively)

FIG. 2: Preferred nucleotide sequence for the theta subunit, together with its deduced amino acid sequence corresponding thereto (SEQ.ID.NO.3 and SEQ.ID.NO.4, respectively).

Figure 3:
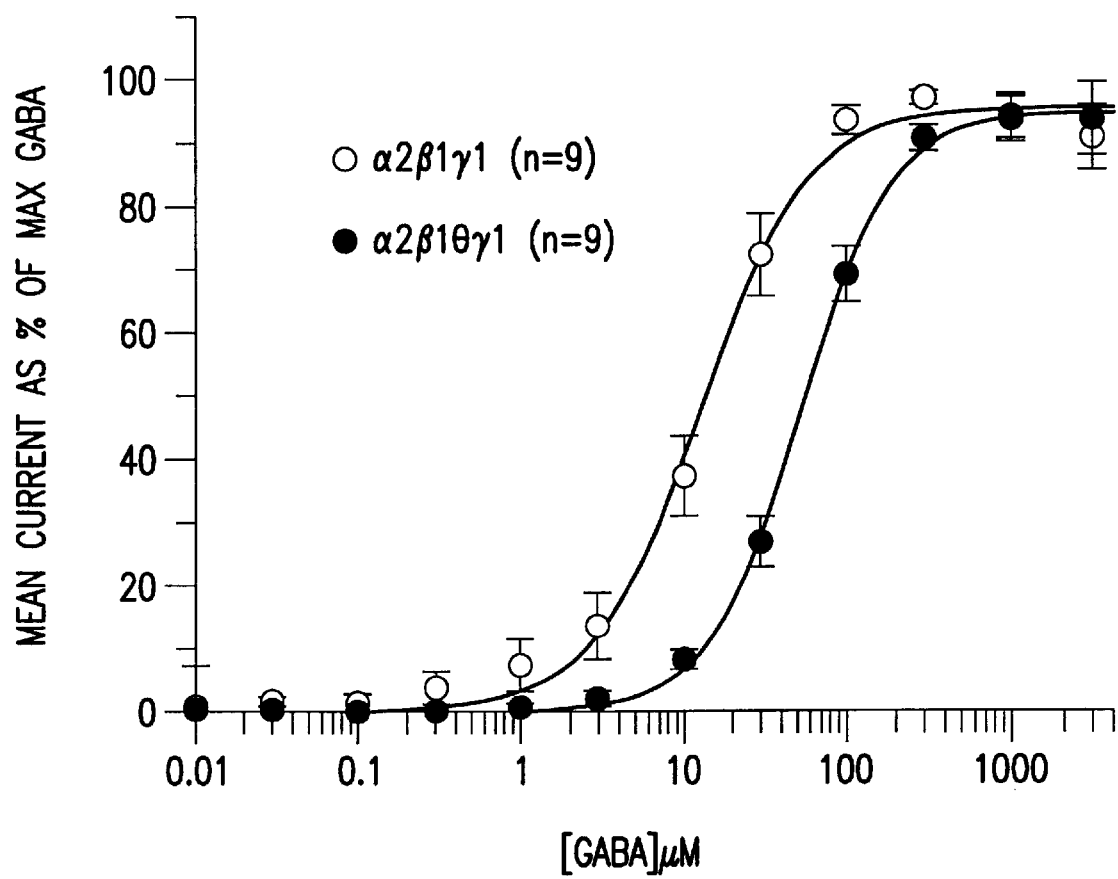
FIG. 3: GABA dose-response curves on HEK cells transiently transfected with and without θ subunit-containing GABA-A receptors ($\beta_2\beta_1\theta\gamma_1$ and $\alpha_2\beta_1\gamma_1$).

The following non-limiting Examples illustrate the present invention.

EXAMPLE 1

ISOLATION AND SEQUENCING OF A cDNA ENCODING THE HUMAN GABA$_A$ RECEPTOR θ SUBUNIT

The Genbank database was searched with GABA$_A$ receptor polypeptide amino acid sequences using the BLAST searching algorithm, and a number of homologous sequences identified. One of these U47334 was investigated in more detail. U47334 contained sequences homologous to part of the amino-terminal extracellular domain and the TM4 spanning domain of other GABA$_A$ receptor subunits, but did not appear to contain any sequence homologous to the regions spanning these domains. Polymerase chain reaction (PCR) was performed to determine if the size if the U47334 sequence was correct, or was for example, the result of an incorrect splicing event. For PCR, a sense (5' gcaaatgaagctgtggttc 3') (SEQ.ID.NO. 5) and antisense (5' caaatgttgaacaacccaaag 3') (SEQ.ID.NO. 6) primer were generated from the U47334 sequence, and PCR performed using standard conditions (Whiting et al, PNAS) using human whole brain cDNA (Clontech) as a template. A second PCR reation was then performed using nested sense (5' gcctgagaccgaattttgg 3') (SEQ.ID.NO. 7) and antisense (5' ggaaccgggaccacttgtc 3') (SEQ.ID.NO. 8) primers generated from the U47334 sequence, and using the products from the first PCR as a template. A single PCR product of approximately 1600 bp was obtained suggesting that the U47334 sequence represents an incorrectly processed message. This product was sequenced directly using an Applied Biosystems 373 DNA sequencer and dye terminator chemistry.

cDNA sequences 5' and 3' of the U47334 sequence were obtained by 5'- and 3'-anchored PCR using human brain Marathon cDNA cloning kit (Clontech) according to the manufacturer's protocols. The nested antisense (5' tagtccagggtcaagttc 3' and 5' tagtatgctaagcgtgaatc 3') (SEQ.ID.NOS. 9 and 10) and sense (5' gagtttgaggatagttgc 3' and 5' tgctccttcactgaaggg 3') (SEQ.ID.NOS. 11 and 12) primers were derived from both the U47334 sequence and the sequence from the initial PCR amplifications. The PCR products were sequenced directly as previously described.

A full length cDNA was generated by PCR using primers derived from sequences downstream of the innitiating ATG (5' ccatgactcaagcttgccaccatgctgcgagccgeagtgatc 3', incorporating a HindIII site) (SEQ.ID.NO. 13) and in the 3' UT of the anchored PCR product (5' tgaaaggagcacagcacagtgctcccg 3') (SEQ.ID.NO. 14). The PCR product (1958 bp) was cloned into pMOS (Amersham), subcloned into pCDNAI Amp (Invitrogen), and sequenced completey on both strands by primer walking. Sequence analysis was performed using Inherit (Applied Biosystems), Sequencher (Genecodes), and Genetics Computer Group (Univ. Wisconsin) computer programs.

The coding region encodes 627 amino acids and has all the structural motifs expected of a ligand gated ion channel subunit. Comparison with other ligand gated ion channel subunits indicates that it is most similar to GABA$_A$ receptor subunits, the highest homology being with the $\beta_1$ subunit (45% identity). However, this sequence identity is sufficiently low as to indicate that the new subunit cannot be classified as a fourth human β subunit, but represents a novel class of subunit, classified as θ, within the GABA receptor gene family.

EXAMPLE 2

LOCALISATION OF THE θ SUBUNIT IN MONKEY BRAIN BY IN SITU HYBRIDISATION

Antisense oligonucleotide probes to the human θ subunit sequence were generated on an Applied Biosystems Automated DNA synthesiser Probe 1 5' CTG-CTT-CTT-GCA-CAC-CCT-TCT-CGC-CAT-GGT-GAA-GCA-TGG-GCT-TCC 3' (SEQ.ID.NO. 15) Probe 2 5'TGT-CGC-CTA-GGC-TGG-CGC-CGA-GGT-CCT-CGA-CTG-TAG-AAA-AGA-TAG 3' (SEQ.ID.NO. 16)

Each oligonucleotide was 3'-end labelled with [$^{35}$S] deoxyadenosine 5'-(thiotriphosphate) in a 30:1 molar ratio of $^{35}$S-isotope:oligonucleotide using terminal deoxynucleotidyl transferase for 15 min at 37° C. in the reaction buffer supplied. Radiolabelled oligonucleotide was separated from unincorporated nucleotides using Sephadex G50 spin columns. The specific activities of the labelled probes in several labelling reactions varied from 1.2–2.3×10$^9$ cpm/mg. Monkey brains were removed and fresh frozen in 1 cm blocks. 12 μm sections were taken and fixed for in situ hybridisation. Hybridisation of the sections was carried out according to the method of Sirinathsingji and Dunnett (Imaging gene expression in neural graft; *Molecular Imaging in Neuroscience*: A Practical Approach, N. A. Sharif (ed), Oxford University Press, Oxford, pp43–70, 1993). Briefly, sections were removed from alcohol, air dried and 3×10$^5$ cpm of each $^{35}$S-labelled probe in 100 μl of hybridisation buffer was applied to each slide. Labelled "antisense" probe was also used in the presence of an excess (100×) concentration of unlabelled antisense probe to define non-specific hybridisation. Parafilm coverslips were placed over the sections which were incubated overnight (about 16 hr) at 37° C. Following hybridisation the sections were washed for 1 hr at 57° C. in 1×SSC then rinsed briefly in 0.1×SSC, dehydrated in a series of alcohols, air dried and exposed to Amersham Hyperfilm max X-ray film and the relative distribution of the mRNA assessed for a variety of brain regions.

Messenger RNA for the subunit was seen in components of the limbic system (involved in emotions such as rage, fear, motivation sexual behaviours and feeding) ; medial septum, cingulate cortex, the amygdala and hippocampal fields (dentate gyrus, CA3, CA2, CA1) and in various hypothalamic nuclei (often associated with the limbic system). Messenger RNA was also present in regions that have been associated with pain perception; the cingulate cortex, insular cortex, and in mid brain and pons structures (e.g. central grey and reticular formation).

EXAMPLE 3

LOCALISATION OF THE θ SUBUNIT IN MONKEY BRAIN BY WESTERN BLOT ANALYSIS AND IMMUNOCYTOCHEMISTRY

Antibodies to the human GABA$_A$ Theta subunit were generated by sub-cutaneous injection of two New Zealand White rabbits with a glutathione-S-transferase (GST) fusion protein consisting of residues 353–595 of the large cytoplasmic loop region of the theta subunit. DNA encoding this region was cloned into the bacterial expression vector pGEX-2T (Pharmacia), transformed into *E. coli* DH10B cells (Life Technologies), and expression of the fusion protein was carried out using the Pharmacia protocols. The bacterial cells were incubated on ice in STE solution (150 mM NaCl, 10 mM Tris-HCl pH 8, 1 mM EDTA) containing 100 μg/ml Lysozyme for 20 min before the addition of N-lauryl sarkosine to 1.5% (w/v). The bacterial slurry was sonicated on ice, and any insoluble matter removed by centrifugation. Triton X-100 was added to 3% (v/v) final and the GST-fusion protein purified by glutathione-agarose affinity chromatography. Columns were washed extensively with PBS and the bound protein eluted with 20 mM free glutathione in 150 mM NaCl, 100 mM Tris-HCl pH 9, 1 mM EDTA, 1 mM Dithiothreitol. Eluted protein was concentrated by precipitation with 5 volumes of cold acetone, resuspended in water, and stored at −70° C. until use.

For western blot analysis tissue samples were removed and dissected out on a glass plate at 4° C. The tissue was homogenised in 50 mM Tris, pH 7.5, containing 1 mM PMSF, 1 μM pepstatin A. The homogenate was centrifuged (2000×g) for 10 minutes and the supernatant was centrifuged at 20,000×g for 45 minutes. The pellet was resuspended in 50 mM Tris and recentrifuged. The final pellet was resuspended in 50 mM Tris pH 7.4 containing protease inhibitors and detergent (Na-deoxycholate:0.25%, 150 mM NaCl, 1 mM EDTA, 1 mM PMSF, 1 μM pepstatin and leupeptin. Membrane preparations were separated on a 10% Tris tricine polyacrylamide gel and electrophoretically transferred to nitrocellulose. Nitrocellulose was blocked with 5% non-fat milk (marvel™)/PBS/Tween (0.5%) for 1 hour at room temperature. The anti θ subunit antibody was used at a concentration of 1:500 made up in PBS/Tween/milk at 4° C. overnight, washed and then incubated with anti-rabbit IgG HRP linked (Amersham) at 1:1000 in PBS/Tween/milk for one hour at room temperature. The filters were washed, incubated in ECL (Amersham) for 1 min and opposed to film. A single band of approximately 60–66 kDa was visualised in brainstem and striatal membranes, close to the predicted molecular weight for the θ subunit of 68–74 kDa.

For localisation of the θ subunit by immunocytochemistry a rhesus monkey was deeply anesthetised with ketamine and sodium pentobarbitone and transcardially perfused with saline, followed by 10% formal saline. The brain was removed, post fixed for 24 hours, and sliced into coronal blocks, which were then dehydrated through graded alcohols, cleared and embedded in paraffin wax. Coronal sections (8 μm) were cut on a base sledge microtome and mounted on glass microscope slides. Sections were deparaffinised, rehydrated and rinsed in 0.1M phosphate buffered saline (PBS). In order to enhance the immunoreactivity sections were subjected to antigen retrieval techniques. Briefly, sections were placed in 0.1M citrate buffer pH 6.0 and given two 5 minute bursts at full power in a conventional microwave oven (800 W). Once rinsed in PBS, sections were incubated in 5% normal goat serum in PBS, for 1 hr to block background staining. Sections were then incubated overnight at +4° C. in the anti θ subunit rabbit polyclonal antibody (1:1000 diluted in blocking buffer). Immunoreactivity was visualised using the Vector eliltem system (Vector Laboratories, Peterborough, U.K.), followed by development in diaminobenzidine (DAB) (Sigma, U.K.). Sections were counterstained in Gill's haematoxylin (Biomen, High Wycombe, U.K.), dehydrated and mounted for microscopical examination. For comparison, samples of 10% formalin immersion fixed post mortem human brainstem were processed in an identical manner. Comparable sections were used to detect θ subunit and tyrosine hydroxylase (Institut Jacques Boy, Reims, France) immunoreactivity by the application of $^{35}$S-labeled goat anti rabbit immunoglobulin 1:100 (Amersham Life Sciences, U.K.) for 1 hr. Slides were rinsed in distilled water, dehydrated to 95% ethanol, air dried and exposed to Amersham Hyperfilm βmax. Sections used for the immunofluorescent colocalisation of θ subunit and tyro sine hydroxylase were pretreated in the same manner, anti θ subunit immunoreactivity was detected using firstly a biotinylated anti rabbit; 1:200 (Vector Laboratories) followed by FITC conjugated streptavidin (Sigma, U.K.). The second rabbit polyclonal serum, anti tyrosine hydroxylase, was again visualised using biotinylated anti rabbit, reacted with Cy3 conjugated strepavidin (Sigma, U.K.). Sections were counterstained with Hoescht 33258 (0.5 μg/ml). To avoid any crossreactivity of the detection systems, sections were placed in boiling distilled water for 5 minutes prior to the application of the second primary antibody and its subsequent detection. The distribution of the θ subunit immunoreactivity in monkey brain reflected the distribution of the θ mRNA observed by in situ hybridisation studies (Example 2). Labelled neurons were observed of hypothalamic and cortical pyramidal neurones. Significant labellingwas observed of cells in the brainstem, including the substantia nigra pars compacta, ventral and lateral tegmental areas, pigmented neurones of the locus coeruleus and restricted population within the dorsal raphe. Labelling of cell terminals within the caudate putamen was also observed. This distribution was found to closely resemble the distribution of tyrosine hydroxylase immunoreactivity, a marker of catocholaminergic neurones and their processes, visualised by immunoautoradiography. θ subunit colocalisation with tyrosine hydroxylase containing neurons was confirmed, using combination immunofluorescence. The expression of the θ subunit seen in both the catocholaminergic neurons of the substantia nigra pars compacta and locus coeruleus was further substantiated in sections of human post mortem brainstem.

EXAMPLE 4

CONSTRUCTION OF AN LTK⁻CELL LINE EXPRESSING THE THETA RECEPTOR SUBUNIT

A chimeric construct of the theta subunit was constructed in the mammalian expression vector pcDNA3.1Zeo (Invitrogen) that consisted of bases −224 to +99 of bovine $GABA_A$ α1 gene, a sequence encoding the c-myc epitope tag (residues 410–419 of the human oncogene product c-myc), a cloning site encoding the amino acids aparagine—serine—glycine, and DNA encoding residues 22–627 of the $GABA_A$ θ gene product. This construct was linearised and the DNA transfected into a clonal population of mouse Ltk⁻ cells that had previously been shown to be stably transfected with the $GABA_A$ receptor subunits $\alpha_2\beta_1\gamma_1$ and separately an Ltk⁻ line stably transfected with $\alpha_2\beta_3\gamma_2$. The resultant cells were clonally selected with Zeocin selection (100 μg/ml), and screened to verify stable intrgration and expression of $\alpha_2\beta_1\theta\gamma_1$ and $\alpha_2\beta_3\theta\gamma_2$ respectively.

EXAMPLE 5

WHOLE CELL PATCH-CLAMP OF HEK 293 CELLS TRANSIENTLY TRANSFECTED WITH HUMAN GABA-A RECEPTORS

Experiments were performed on HEK 293 cells transiently transfected with human cDNA combinations $\alpha_2\beta 1\gamma 1$, and α2β1θγ1 (4 μgs of cDNA total per cover-slip) using calcium phosphate precipitation (Chen and Okayama, 1988) as previously described (Hadingham et al, 1993). Glass cover-slips containing the cells in a monolayer culture were transferred to a perspex chamber on the stage of Nikon Diaphot inverted microscope. Cells were continuously perfused with a solution containing 124 mM NaCl, 2 mM KCl, 2 mM $CaCl_2$, 1 mM $MgCl_2$, 1.25 mM $KH_2PO_4$, 25 mM $NaHCO_3$, 11 mM D-glucose, at pH 7.2, and observed using phase-contrast optics. Patch-pipettes were pulled with an approximate tip diameter of 2 μm and a resistance of 4MΩ with borosilicate glass and filled with 130 mM CsCl, 10 mM HEPES, 10 mM EGTA, 3 mM $Mg^+$-ATP, pH adjusted to 7.3 with CsOH. Cells were patch-clamped in whole-cell mode using an Axopatch 200B patch-clamp amplifier. Drug solutions were applied by a double-barrelled pipette assembly, controlled by a stepping motor attached to a Prior manipulator, enabling rapid equilibration around the cell. Increasing GABA concentrations were applied for 2 sec pulses with a 30 sec interval between applications. Non-cumulative concentration-response curves to GABA were constructed. Curves were fitted using a non-linear square-fitting program to the equation $f(x)=B_{MAX}/[1+(EC_{50}/x)^n]$ where x is the drug concentration, $EC_{50}$ is the concentration of drug eliciting a half-maximal response and n is the Hill coefficient. $EC_{50}$'s were analysed by unpaired students t-test.

The GABA $EC_{50}$ of HEK 293 cells transiently expressing the $GABA_A$ receptor subunit combination $\alpha_2\beta_1\theta\gamma_1$ is significantly lower than that of HEK 293 cells transiently expressing the $GABA_A$ receptor subunit combination $\alpha_2\beta_1\gamma_1$ (see FIG. 3).

|  | $\alpha_2\beta_1\gamma_1$ | $\alpha_2\beta_1\theta\gamma_1$ |
|---|---|---|
| $EC_{50}$ | 16.7 ± 3.7 nM | 62.7 ± 6.7 nM* |
| Slope | 1.6 ± 0.2 | 1.5 ± 0.1 |

*p < 0.001

---

What is claimed is:

1. A stably co-transfected eukaryotic cell line capable of expressing a human $GABA_A$ receptor, which receptor comprises a θ receptor subunit of SEQ ID NO:4 and at least one receptor subunit.

2. A cell line according to claim 1 which is a rodent fibroblast cell line.

3. A process for the preparation of an eukaryotic cell line capable of expressing a human $GABA_A$ receptor, which comprises stably co-transfecting a eukaryotic host cell with at least two expression vectors, one such vector comprising the cDNA sequence encoding the human θ $GABA_A$ receptor subunit of SEQ ID NO:4 and one such vector comprising the cDNA sequence encoding an α $GABA_A$ receptor subunit.

4. A process according to claim 3 wherein the cell line is a rodent fibroblast cell line.

5. A recombinant nucleic acid molecule encoding the θ subunit of the human $GABA_A$ receptor comprising a sequence selected from the group consisting of the sequence depicted in SEQ ID NO:3; the complement of said sequence, and sequences having at least 95% homology to SEQ ID NO:3 or its complement, wherein a human $GABA_A$ receptor having the subunit combination $\alpha_2\beta_1\theta_1\gamma_1$ has a lower affinity for GABA as compared to a human $GABA_A$ receptor having the subunit combination $\alpha_2\beta_1\gamma_1$.

6. A recombinant expression vector comprising a human $GABA_A$ receptor θ subunit nucleotide sequence selected from the group of SEQ ID NO:3, the complement of said sequence, and sequences having 95% homology to SEQ ID NO: 3 or its complement, together with additional sequences capable of directing the synthesis of said human $GABA_A$ receptor θ subunit in cultures of transfected eukaryotic cells, wherein a human $GABA_A$ receptor having the subunit combination $\alpha_2\beta_1\theta_1\gamma_1$ has a lower affinity for GABA as compared to a human $GABA_A$ receptor having the subunit combination $\alpha_2\beta_1\gamma_1$.

7. A recombinantly produced protein preparation comprising a $GABA_A$ receptor having subunit combinations comprising a θ receptor subunit of SEQ ID NO:4 and at least one a receptor subunit.

8. A recombinantly produced membrane preparation comprising a $GABA_A$ receptor having subunit combinations comprising a θ receptor subunit of SEQ ID NO:4 and at least one α receptor subunit.

9. A preparation according to claim 7 wherein the subunit combination derived is selected from the group consisting of the $\alpha_1\theta\gamma_2$, $\alpha_2\beta_1\theta\gamma_1$ or $\alpha_2\beta_3\theta\gamma_2$ subunit combination of the $GABA_A$ receptor.

10. A method for determining whether a ligand, not known to be capable of binding to a human $GABA_A$ receptor comprising a θ subunit, can bind to a human $GABA_A$ receptor comprising a θ subunit, which comprises (a) contacting a mammalian cell comprising DNA molecules encoding at least one a receptor subunit and a θ receptor subunit of SEQ ID NO:4 with the ligand under conditions permitting binding of ligands known to bind to the $GABA_A$ receptor, (b) detecting the presence or absence of any of the ligand bound to the $GABA_A$ receptor comprising a θ subunit and (c) thereby determining whether the ligand binds to the $GABA_A$ receptor comprising a θ subunit.

11. A method of screening drugs to identify drugs which specifically interact with, and bind to, a human $GABA_A$ receptor comprising a θ subunit on the surface of a cell which comprises (a) contacting a mammalian cell comprising a human $GABA_A$ receptor comprising at least one α receptor subunit and a θ receptor subunit of SEQ ID NO:4, on the surface of said cell with a plurality of drugs, (b) determining which of those drugs bind to the mammalian cell, and (c) thereby identifying drugs specifically interact with, and bind to, human $GABA_A$ receptors comprising the θ subunit.

12. A recombinant GABA$_A$ receptor θ subunit polypeptide which has an amino acid sequence depicted in SEQ ID NO:4.

13. A preparation according to claim 8 wherein the subunit combination derived is the $\alpha_1\theta\gamma_2$, $\alpha_2\beta_1\theta\gamma_1$ or $\alpha_2\beta_3\theta\gamma_2$ subunit combination of the GABA$_A$ receptor.

14. A stably co-transfected eukaryotic cell line which expresses a human GABA$_A$ receptor, which receptor comprises the subunit combination $\alpha_2\beta_1\theta\gamma_1$, wherein the θ receptor subunit has the sequence of SEQ ID NO:4.

15. A cell line according to claim 14 which is a rodent fibroblast cell line.

16. A process for the preparation of an eukaryotic cell line capable of expressing a human GABA$_A$ receptor, said receptor comprising the subunit combination $\alpha_2\beta_1\theta\gamma_1$, wherein said θ receptor subunit has the sequence depicted in SEQ ID NO:4, said process comprising stably co-transfecting a eukaryotic host cell with at least two expression vectors, one such vector comprising the cDNA sequence encoding the human θ GABA$_A$ receptor subunit and one such vector comprising the cDNA sequence encoding an alpha GABA$_A$ receptor subunit.

17. A process according to claim 16 wherein the cell line is a rodent fibroblast cell line.

18. A recombinant nucleic acid molecule encoding the θ subunit of the human GABA$_A$ receptor, said θ subunit having the sequence depicted in SEQ ID NO:4.

19. A recombinant expression vector comprising the nucleotide sequence of the human GABA$_A$ receptor theta subunit sequence depicted in SEQ ID NO:4, together with additional sequences capable of directing the synthesis of the said human GABA$_A$ receptor θ subunit in cultures of transfected eukaryotic cells.

20. A recombinantly produced protein preparation comprising a GABA$_A$ receptor having the subunit combination $\alpha_2\beta_1\theta\gamma_1$, wherein said θ receptor subunit has the sequence depicted in SEQ ID NO:4.

21. A recombinantly produced membrane preparation comprising a GABA$_A$ receptor having the subunit combination $\alpha_2\beta_1\theta\gamma_1$, wherein said θ receptor subunit has the sequence depicted in SEQ ID NO:4.

22. A method for determining whether a ligand not known to be capable of binding to a human GABA$_A$ receptor can bind to said receptor, said receptor having the subunit combination $\alpha_2\beta_1\theta\gamma_{12}$, wherein said θ receptor subunit has the sequence depicted in SEQ ID NO:4, which method comprises (a) contacting a mammalian cell expressing a human GABA$_A$ receptor having the subunit combination $\alpha_2\beta_1\theta\gamma_1$, wherein said θ receptor subunit has the sequence depicted in SEQ ID NO:4, with the ligand under conditions permitting binding of ligands known to bind to the GABA$_A$ receptor, (b) detecting the presence or absence of any of the ligand bound to the GABA$_A$ receptor comprising the θ subunit and (c) thereby determining whether the ligand binds to the GABA$_A$ receptor.

23. A method of screening drugs to identify drugs which specifically interact with, and bind to, a human GABA$_A$ receptor on the surface of a cell, the receptor having the subunit combination $\alpha_2\beta_1\theta\gamma_1$, wherein said θ receptor subunit has the sequence depicted in SEQ ID NO:4, which method comprises (a) contacting a mammalian cell expressing a human GABA$_A$ receptor having the subunit combination $\alpha_2\beta_1\theta\gamma_1$, wherein said θ receptor subunit has the sequence depicted in SEQ ID NO:4, on the surface of said cell with a plurality of drugs, (b) determining which of those drugs bind to the mammalian cell, and (c) thereby identifying drugs specifically interact with, and bind to, the human GABA$_A$ receptor.

24. A recombinant GABA$_A$ receptor theta subunit polypeptide which has an amino acid sequence depicted in SEQ ID NO:4.

* * * * *